United States Patent
Lin et al.

(10) Patent No.: US 9,433,803 B2
(45) Date of Patent: Sep. 6, 2016

(54) METHOD AND SYSTEM FOR DESTROYING ADIPOSE TISSUE NON-INVASIVELY AND ACCELERATING LIPID METABOLISM

(71) Applicants: National Health Research Institutes, Zhunan Town, Miaoli County (TW); National Cheng Kung University, Tainan (TW)

(72) Inventors: Chou-Ching Lin, Tainan (TW); Gin-Shin Chen, Miaoli County (TW)

(73) Assignees: National Health Research Institutes, Zhunan Town (TW); National Cheng Kung University, Tainan (TW)

( * ) Notice: Subject to any disclaimer, the term of this patent is extended or adjusted under 35 U.S.C. 154(b) by 132 days.

(21) Appl. No.: 14/052,473

(22) Filed: Oct. 11, 2013

(65) Prior Publication Data

US 2014/0107535 A1    Apr. 17, 2014

Related U.S. Application Data

(60) Provisional application No. 61/713,121, filed on Oct. 12, 2012.

(51) Int. Cl.

| A61N 7/00 | (2006.01) |
|---|---|
| A61N 1/00 | (2006.01) |
| A61N 7/02 | (2006.01) |
| A61N 1/36 | (2006.01) |
| A61N 1/04 | (2006.01) |

(52) U.S. Cl.
CPC . *A61N 7/00* (2013.01); *A61N 1/00* (2013.01); *A61N 1/36003* (2013.01); *A61N 1/36014* (2013.01); *A61N 7/02* (2013.01); *A61N 1/0452* (2013.01); *A61N 2007/0008* (2013.01)

(58) Field of Classification Search
CPC .......... A61N 1/36014; A61N 1/0452; A61N 2007/0008; A61N 7/02; A61N 7/00; A61N 1/00; A61N 1/36003; A61B 2019/464; A61B 2019/5276
See application file for complete search history.

(56) References Cited

U.S. PATENT DOCUMENTS

| RE38,030 E * | 3/2003 | Chapelon et al. ............ 600/439 |
|---|---|---|
| 7,258,674 B2 | 8/2007 | Cribbs et al. |

(Continued)

OTHER PUBLICATIONS

F.A. Taran, et al.; "Magnetic resonance-guided focused ultrasound (MRgFUS) compared with abdominal hysterectomy for treatment of uterine leiomyomas" for the MRgFUS group. Ultrasound in Obstetrics and Gynecology, 2009.

(Continued)

*Primary Examiner* — Bo J Peng
(74) *Attorney, Agent, or Firm* — Knobbe, Martens, Olson & Bear, LLP (57) ABSTRACT

The present disclosure is to destroy adipose tissue non-invasively by using focused ultrasound (FUS) and to increase the treatment efficiency by the synergy of the novel FUS and electrical stimulation. Lipid can be released from the destroyed adipocytes and stay in the interstitial fluid of undestroyed adipocytes. In the meanwhile or after the treatment of FUS, a passive exercise of muscle in thighs or other parts is performed by electrical stimulation to consume energy. Therefore, metabolism of the free lipid can be enhanced by supplying energy to the muscles. The ultrasound treatment of the present disclosure is able to increase the treatment area, and while in combination with electrical stimulation, it can efficiently remove lipids in the circulation.

19 Claims, 5 Drawing Sheets

(56) References Cited

U.S. PATENT DOCUMENTS

| | | | |
|---|---|---|---|
| 7,875,023 B2 | 1/2011 | Eshel et al. | |
| 2005/0251120 A1* | 11/2005 | Anderson | A61B 5/6804 606/20 |
| 2007/0032726 A1* | 2/2007 | Osaka | A61B 5/0048 600/459 |
| 2007/0055154 A1* | 3/2007 | Torbati | A61H 23/0245 600/439 |
| 2007/0239075 A1* | 10/2007 | Rosenberg | A61N 1/0408 601/2 |
| 2008/0015435 A1 | 1/2008 | Cribbs et al. | |
| 2008/0255478 A1* | 10/2008 | Burdette | A61N 7/02 601/2 |
| 2009/0230822 A1* | 9/2009 | Kushculey | A61N 7/02 310/366 |
| 2009/0287264 A1* | 11/2009 | Paret | 607/3 |
| 2010/0160782 A1* | 6/2010 | Slayton | A61B 5/4869 600/439 |
| 2012/0004548 A1* | 1/2012 | Eshel et al. | 600/439 |
| 2013/0012840 A1* | 1/2013 | Feferberg | 601/2 |

OTHER PUBLICATIONS

A. Okada, et al., Non-invasive magnetic resonance-guided focused ultrasound treatment of uterine fibroids in a large Japanese population: impact of the learning curve on patient outcome Ultrasound in Obstetrics & Gynecology, 2009.

A. Dobrotwir and E. Pun, "Clinical 24 month experience of the first MRgFUS unit for treatment of uterine fibroids in Australia" Journal of Medical Imaging and Radiation Oncology, 2012.

E. Garcia-Murray, et al., "Evaluation of the Acute and Chronic Systemic and Metabolic Effects from the Use of High Intensity Focused Ultrasound for Adipose Tissue Removal and Non-Invasive Body Sculpting" American Society of Plastic Surgeons Annual Meeting, 2005.

A. Fatemi, "High-Intensity Focused Ultrasound Effectively Reduces Adipose Tissue" Seminars in Cutaneous Medicine and Surgery, 2009.

S.A. Teitelbaum et al., Plastic and Reconstructive Surgery, Sep. 2007.

* cited by examiner

METHOD AND SYSTEM FOR DESTROYING ADIPOSE TISSUE NON-INVASIVELY AND ACCELERATING LIPID METABOLISM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

1. Technical Field

The disclosure relates to the non-invasive destruction of adipose tissue by using focused ultrasound (FUS). The present disclosure also relates to the improvement in treatment efficiency of the novel FUS by the combination with electrical stimulation.

2. Description of Related Art

Obesity and overweight have been clinically identified as a cause of many diseases, such as hypertension, cardiovascular diseases, and type-2 diabetes. Body Mass Index (BMI) is a measurement of obese degree and people are defined as overweight if their BMI is between 25 and 30 kg/m2, and obese when it is greater than 30 kg/m2. Centers for Disease Control and Prevention of USA report that 33.8% of U.S. adults are obese and approximately 17% (or 12.5 million) of children and adolescents aged 2-19 years are obese in 2007-2008. Moreover, obesity trend among U.S. adults is a dramatic increase from 1985 through 2010, and no state had a prevalence of obesity less than 20% in 2010 (http://www.cdc.gov/obesity/index.html).

Adipose tissue is composed of fat cells (adipocytes) in which the lipid is stored. Liposuction surgery has been used to break fat cells and then to remove the lipid by suction. However, liposuction surgery is an invasive surgery with high risk, and it needs several weeks of recovery time.

Recently, a noninvasive tumor treatment by using high-intensity focused ultrasound (HIFU) is established and affirmed clinically. In particular, said treatment for uterine fibroids is approved by the FDA in the U.S. The principles of said treatment are that the acoustic beam is generated extracorporeally by an ultrasound transducer, transmitted via a plurality of media and focused on the target region, and the high energy within the focus can be absorbed by tumor cells to form a hot spot. The temperature of the hot spot is up to 60-70° C. to cause coagulative necrosis of the tumor cells during a short time period. The necrosed cells can be cleaned naturally after treatment. Clinical trials show that more than 6,000 female patients worldwide who suffered from uterine fibroids have been treated by HIFU. Based on the treatment results and trace after surgery, the safety, effectiveness and reliability of HIFU for noninvasive tissue ablation is confirmed (F. A. Taran, et al.; for the MRgFUS group. Ultrasound in Obstetrics and Gynecology, 2009; A. Okada, et al., Ultrasound in Obstetrics & Gynecology, 2009; A. Dobrotwir and E. Pun, Journal of Medical Imaging and Radiation Oncology, 2012).

Tissue ablation by HIFU modality has been applied to cosmetic body sculpting, such as U.S. Patent Pub. No. 20080015435, which discloses a HIFU system for the destruction of adipose tissue in the human body. The system contains a plurality of sensors adopted to detect echo signals created by cavitation or boiling of organic tissue for the safety of ablation treatment. Further, a transducer of the system emits ultrasonic waves with a specific sequence of on/off cycles into organic tissue, such that heat produced at the target is not easy to be conducted away between consecutive on cycles in the sequence. The system can detect fat thickness by optical cameras and ultrasonic imaging system.

Safety of adipose cell ablation by HIFU has been confirmed in clinical trial (E. Garcia-Murray, et al., American Society of Plastic Surgeons Annual Meeting, 2005). Twenty-four patients underwent the HIFU treatment and had blood drawn at various time points as follows: before HIFU treatment, after HIFU treatment including 1, 2 and 3 day, 1-4 weeks and 1-3 months later. The blood analyses illustrate no significant changes in the level of free fatty acids, total cholesterol, very low density lipoprotein (VLDL), high density lipoprotein (HDL), low density lipoprotein (LDL) and triglyceride. At the same time, comprehensive metabolic panel, amylase, lipase and complete blood count of the 24 patients have no significant variation. Accordingly, it is believed that removing adipose tissue by HIFU can't cause acute or chronic side effect of metabolisms of lipid, free fatty acid and glucose as well as functions of liver and kidney.

With respect to therapeutic outcome, the clinical trial reports that 282 patients with average 41.3-year-old are treated by HIFU once with 45-60 minutes of treating time, and their waistline reduced 4.7 cm in average within 3 months (A. Fatemi, Seminars in Cutaneous Medicine and Surgery, 2009). The mechanism of said treatment is that HIFU destroyed a part of adipose cells to release lipid, and the destroyed cells stay with undestroyed adipose cells. In about 8 weeks later, scavenger macrophages engulf the intercellular lipids. However, about 75% of the released lipid is re-absorbed by the undestroyed adipose cells (P. B. Fodor, et al., American Society for Aesthetic Plastic Surgery Annual Meeting, 2006).

Cavitation induced by ultrasound is also used in destroying adipose tissue. Distinctive from thermal ablation of HIFU, ultrasonic cavitation generates bubble collapse within adipose tissue to destroy it. As described in U.S. Pat. No. 7,875,023, an apparatus emits a pulsed focused ultrasound with a frequency in a range of 50 KHz-1000 KHz outside of body, directs said ultrasonic energy at a target region, i.e., adipose tissue, and generates cavitation with a duty cycle between 1:2 and 1:250 to lyse adipose tissue.

Pulsed focused ultrasound is used to remove adipose tissue in more than 50 countries and the total number of said treatment is as high as 200 thousand. Safety and effectiveness have been confirmed based on treatment results from 550 patients (http://www.ultrashape.com). Waistline can be reduced 4 cm in average by three-time treatment with 30-90 minutes per treatment. Therapeutic results can be observed in 4 weeks after treatment. It is also confirmed that the released triglyceride from the patient's adipose tissue subject to pulsed focused ultrasound treatment does not significantly accumulate in the blood or liver (S. A. Teitelbaum et al., Plastic and Reconstructive Surgery, September 2007).

Accordingly, it is confirmed that destroying adipose tissue by HIFU or pulsed focused ultrasound treatment can achieve the safety and effectiveness that cosmetic body sculpting possesses. However, it needs to take 2-12 weeks to see the treatment results. Unsuitable dietary habit during this long period can easily reduce the therapy effects. Further, if the released lipid from destroyed adipose tissue is not metabolized, it will be restored to undestroyed or new adipose cells, so that the benefit of ultrasonic therapy is reduced. Further, current ultrasonic transducers can merely focus on a "point" of the target area, which causes the treated area being limited and the treating time being as long as one hour per treatment. It easily makes the patient uncomfortable and restricts the effect of body sculpting.

Lipid is a molecule for storing energy in the body. It is known from the above that the released lipid via ultrasonic treatment may be restored in undestroyed adipose tissue if it is not consumed. The way for enhancing energy consumption includes heat generation and exercise. Exercise can consume energy more efficiently while heat generation cannot be applied frequently due to the accompanying increase of body temperature. Muscle is the main motion organ of the human body and generates contraction under the voluntary control. On the other hand, muscle contraction can be induced by external stimuli like electrical current. External current flows into the body via skin and stimulates near nerves to induce muscle contraction. Since the activation threshold of the muscle is about ten times of that of a nerve, only a small electric current can be used to activate the nerve for safety. While the nerve is activated, action potential is transmitted to neuromuscular junction to trigger the entry of $Ca^{2+}$ into the muscle, and then the interaction of actin and myosin is induced to form muscle contraction. ATP is essential for the interaction of actin and myosin. Maintenance of isometric contraction is an unstable dynamic balance and needs continuous ATP supply, so that a muscle cell has to produce ATP by metabolism of carbohydrates or lipids continuously.

Muscle contraction, as well as energy consumption, induced by self-consciousness control is basically the same as that by external electricity. Therefore, external electricity can be applied to consume energy. Another advantage of energy consumption by muscle contraction, compared with heat generation, is to maintain muscle status or even train the muscle to keep the body fit. Various muscles can be trained by applying electric stimulation to the various parts of muscle.

Transcutaneous electric stimulation is one of standard clinical rehabilitation techniques, which is applied to long-term bedridden patients to avoid muscle disuse atrophy. This technique is never used for increasing energy consumption. Appropriate parameters and electrical stimulation do not harm organisms and muscles or make the patient uncomfortable. Generally, the parameters including the applied electric current per unit of body surface area and the stimulation frequency should be noted. When the applied electric current per unit of body surface area is too high, skin burn may be caused. When the stimulation frequency is too high, muscle fatigue may be caused. Time of treatment is not restricted specifically. However, if ATP consumption rate exceeds ATP generation rate, muscle cell will generate ATP via anaerobic respiration and make the patient feel tired and uncomfortable.

SUMMARY

To solve the above problems, the present disclosure provides a non-invasive system for destroying adipose tissue comprising at least one focused ultrasound device and at least one electrical stimulation device. In one embodiment, the system comprises a plurality of fixers, an ultrasound probe, a power driver, a probe holder, a plurality of electrical stimulators, and a control unit.

The present disclosure also provides a method for destroying adipose tissue comprising the following steps: emitting a focused ultrasound to a target region of a patient, destroying an adipose tissue of the target region by the focused ultrasound, and providing an electrical stimulation to the patient to induce passive exercise of a muscle. The method delivers a synergy of focused ultrasound and electrical stimulation for enhancing the efficiency of destroying adipose tissue, which can be applied to obesity treatment and body sculpting.

In the present disclosure, high-intensity focused ultrasound or pulsed focused ultrasound is used to destroy the adipose tissue.

The method comprises destroying an adipose tissue by noninvasively ultrasound-induced heat (by a high-intensity focused ultrasound) or mechanical force (by a non-thermal ultrasound). High intensity focused ultrasound (HIFU) is a highly precise medical procedure using high-intensity focused ultrasound to heat and destroy pathogenic tissue rapidly. It is demonstrated that tissue heating is proportional to the intensity and the intensity is inversely proportional to the area over which an ultrasound beam is spread. therefore, focusing ultrasound beam into a sharp point (i.e. increasing the beam intensity) may create a rapid temperature rise at the focus. Ultrasound energy creates also mechanical forces independent of thermal effects (i.e., non-thermal effects), thereby causing biologic effects that are not related to temperature rise alone. Non thermal effects are from cavitation, microstreaming and acoustic streaming. Cavitational effects result from the vibration of the tissue causing microscopic air bubbles to form, which transmit the vibrations in a way that directly stimulates cell membranes. The destroyed adipose cells release lipid and stay with undestroyed adipose cells. In the meanwhile or after the treatment of focused ultrasound, a passive exercise of muscle of thigh or other parts is achieved by electrical stimulation, so that calories are consumed and muscle in particular parts can maintain a healthy condition. The method of the present disclosure achieves effective therapy by combining a focused ultrasound technique and an electrical stimulation. Said effective therapy cannot be achieved by any single technique of them.

The present disclosure also provides a system comprising a focused ultrasound probe, a power amplifier for the probe, several pairs of electrodes of electrical stimulation, an electrical stimulator with multi channels, a control unit and a media (such as computer interface). The focused ultrasound probe is composed of one or a plurality of piezoelectric elements, which is driven by the power amplifier to output a high-intensity focused ultrasound (HIFU) or a non-thermal ultrasound. The probe is designed to generate a non-point, line-shape focal zone. At least four micro pressure sensors are disposed in the front side of the probe, which can conduct a real-time detection of applied pressure on human skin by the probe and ensure appropriate contact between the probe and the skin. Further, at least three A-mode ultrasonic transducers are disposed in the probe to conduct a real-time detection of thickness of subcutaneous adipose layer and ensure the ultrasonic focal zone falls within the adipose. The pair of electrodes for electrical stimulation is adhered on any of thighs, shanks, arms, abdomen, waist or back. During or after the ultrasonic treatment, an instruction is input to the control unit through the computer interface, then the electrical stimulator generates an electrical current after receiving the command of the control unit, and the electrical current/stimulation is provided from the pair of electrodes to the target muscle group to achieve a passive exercise. The control unit may also control the ultrasound device to generate noninvasive ultrasound with various output intensities suitable for the target adipose tissue.

One advantage of the present disclosure is the synergy in combination of a focused ultrasound technique and an electrical stimulation. Ultrasound can destroy an adipose tissue non-invasively to release lipid from the treated adipose tissue, and electrical stimulation is able to induce passive exercise of a muscle group to enhance lipid metabolism. The method of the present disclosure is based on the balance of supply-need in human body, so that it is safe undoubtedly. Because of said synergy, the therapeutic effects can be observed in a short time period, and most released lipid is metabolized and not absorbed by undestroyed or new adipose cells.

Another advantage of the present disclosure is that the focused ultrasound probe generates a linear focal region at the geometric focus. In said focal region, HIFU or relatively low-intensity low-frequency non-thermal ultrasound can be generated to burn or burst a larger area of adipose tissue in single shot, so that more lipid is released and treating time is reduced.

Another advantage of the present disclosure is that a plurality of micro pressure sensors are used for real-time detection of pressure on the interface between the probe and skin. Accordingly, the system and the user can know whether the contact between the probe and skin is proper and can ensure smooth propagation of ultrasound to target adipose layer. It can avoid skin burn by the ultrasound from a bad contact. Once the contact is bad during the treatment, the value of pressure can promptly respond, and the system terminates the ultrasonic shot automatically and immediately or the user can push the emergency button to terminate the ultrasonic shot.

Another advantage of the present disclosure is that the design of a plurality of A-mode ultrasonic transducers built in the probe with a constant focal length ensures the ultrasonic focal zone falls within the adipose layer, so that other tissues are not damaged by the treatment. Prior to the ultrasound sonication, the thickness distribution of adipose layer in the direction parallel to the linear focal zone can be obtained by these A-mode ultrasonic transducers. The information of predetermined focal length and measured adipose thickness can ensure the linear ultrasonic focal zone falling within the adipose layer.

DETAILED DESCRIPTION OF THE PREFERRED EMBODIMENT

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
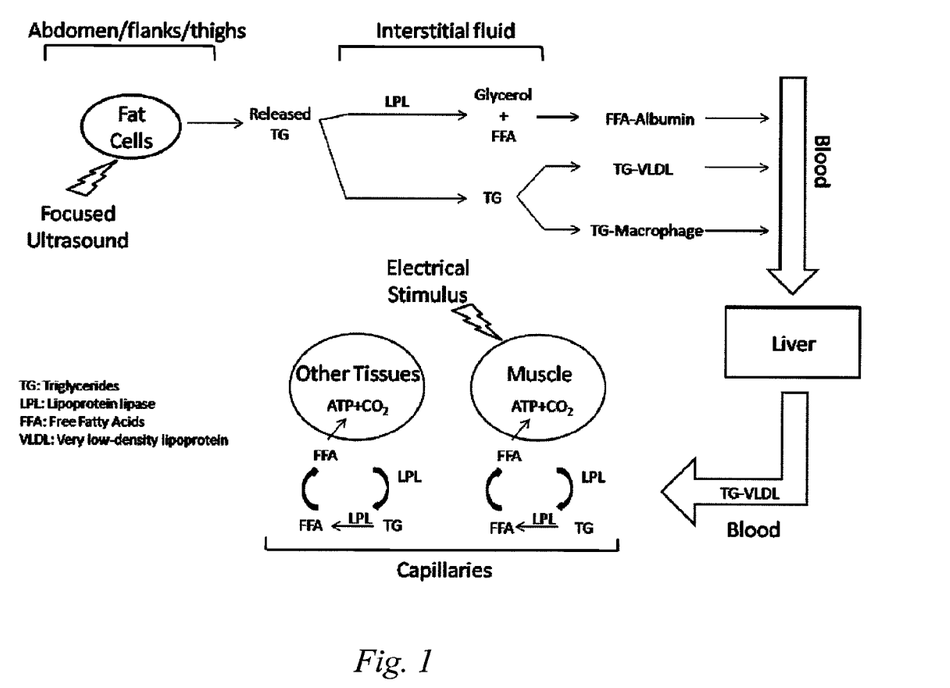
FIG. 1 illustrates the method and mechanism of the treatment of the present disclosure.

The concept of the method of the present disclosure is shown in FIG. 1. While the subcutaneous adipose tissues of the abdomen, waist or thighs are treated by focused ultrasound, triglyceride (TG) is released from the destroyed adipose cell. Released TG stays in intercellular interstitial fluid. Most released TG is decomposed to glycerol and free fatty acids (FFA) by lipoprotein lipase (LPL). Partial non-decomposed TG and partial FFA respectively bind to very low density lipoprotein (VLDL) and albumin, enter into the blood and are transported to the liver. While the muscle groups in the thigh or other parts are treated by electrical stimulation, ATP is consumed by the passive exercise of the muscle groups, and more ATP is needed. At this time, according to the balance of supply-need in the human body, TG-VLDL and FFA-albumin staying in subcutaneous adipose layer are transported to the liver via blood to synthesize TG in a faster metabolism rate (compared with normal metabolism), and the synthesized TG is then transported to the target muscle groups needing more ATP to be consumed. Naturally, blood TG is decomposed to FFA by LPL in blood capillary, and then FFA is decomposed to produce ATP to provide energy to other tissues. Few weeks later, residual TG staying in subcutaneous adipose layer are engulfed and metabolized by macrophages and reabsorbed by undestroyed adipocytes.

Figure 2:
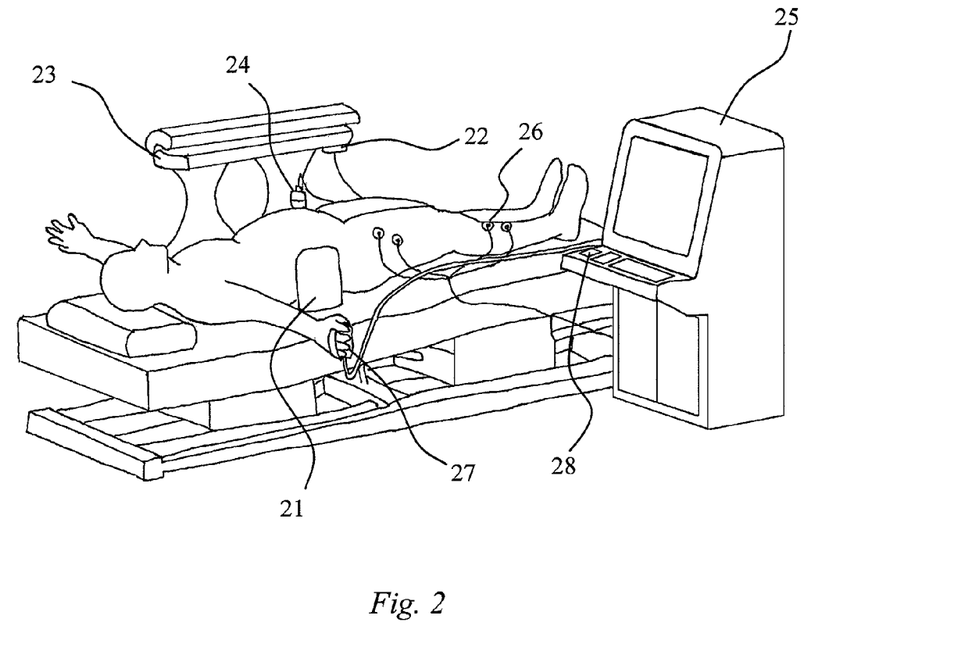
FIG. 2 is a schematic diagram of the general structure and operation of treatment devices constructed and operative in accordance with the synergy of ultrasound therapy and electrical stimulation.

FIG. 2 shows one embodiment of the system of the present disclosure. In particular, FIG. 2 shows one embodiment for abdomen treatment. In the present disclosure, a treatment plan includes movement restriction of the treated part, determination of adipose layer thickness in treatment region, positioning of ultrasonic focal zone, ultrasonic treatment and electrical stimulation. A patient lies on a bed in supine position. Two fixers 21 softly push the patient's flanks from right and left sides, respectively, to make the abdomen tissues bulge slightly, and the fixers 21 are fixed. Accordingly, the abdomen tissues are concentrated, and the shift of treating target caused by respiration or spasmodical jerk can be prevented. Therefore, it can avoid the ultrasonic focal zone from deviating from the target region during the ultrasonic treatment.

After fixing the patient, the probe holder 22 is moved by an operator or by a control system to the treatment site. In some embodiments, the probe holder 22 is moved along a holder track 23 and stopped at a site near the treating target. The hand-held ultrasound probe 24 is used for the next step.

Figure 3A:
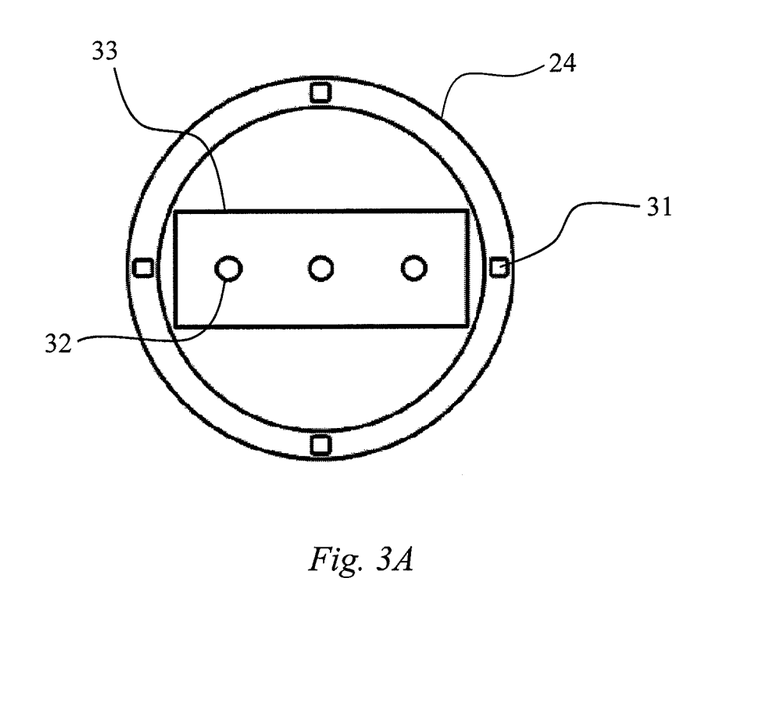
FIG. 3A is a bottom view of the representative ultrasound probe in accordance with the principles of the present disclosure.
Figure 4A:
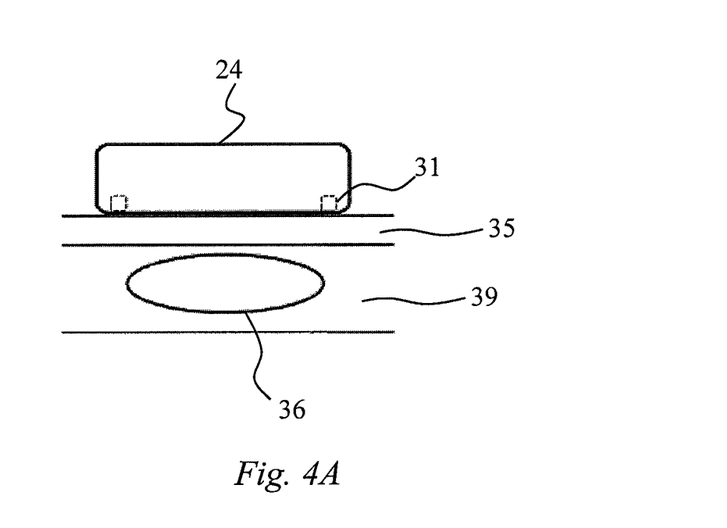
FIGS. 4A and 4B illustrate relationships between the skin/fat tissue layers and position of ultrasonic line-shape focal zone.
Figure 4B:
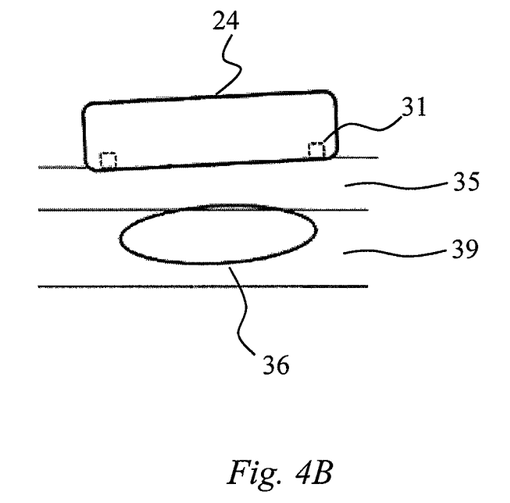

An ultrasonic gel is smeared on the skin before the contact between the ultrasound probe 24 and the skin, so that most ultrasound can be transmitted into the skin. The ultrasound probe 24 is put on the treating target and is slightly pushed down with various directions (i.e., front, back, right, and left). While the pressure values detected by the micro pressure sensors 31 as shown in FIG. 3A are greater than zero (0) and almost identical to each other, namely, it shows well contact between the ultrasound probe 24 and the skin 35, and the linear ultrasonic focal zone 36 being parallel with the skin 35/adipose layer 39 to avoid damage of other tissues (as shown in FIG. 4A, the ultrasound probe 24 is stayed). FIG. 4B illustrates that, while the pressure values are not identical, skin damage may be caused by the partial linear ultrasonic focal zone 36 falling within the skin 35.

Figure 5:
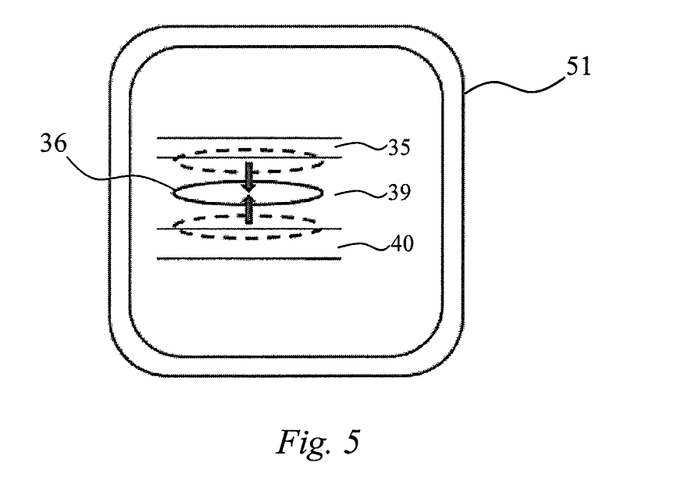
FIG. 5 is a simplified pictorial illustration of the monitor of the control system showing the movement of line-shape focal zone by the actuator in the skin/fat/muscle tissues.

While the ultrasound probe 24 is stayed, the operator observes the thickness and the distribution of the adipose layer on a monitor of the control system 51 by the real-time detection of the A-mode ultrasonic transducers 32 built in the probe 24, as shown in FIG. 3A. Since the depth of ultrasonic focal zone 36 is known and a relevant software is applied, the monitor 51 also shows the relative location of ultrasonic focal zone 36 to the adipose layer 39, as shown in FIG. 5. Therefore, the operator can determine whether ultrasonic focal zone 36 falls within the adipose layer 39 and/or other tissues.

Figure 3B:
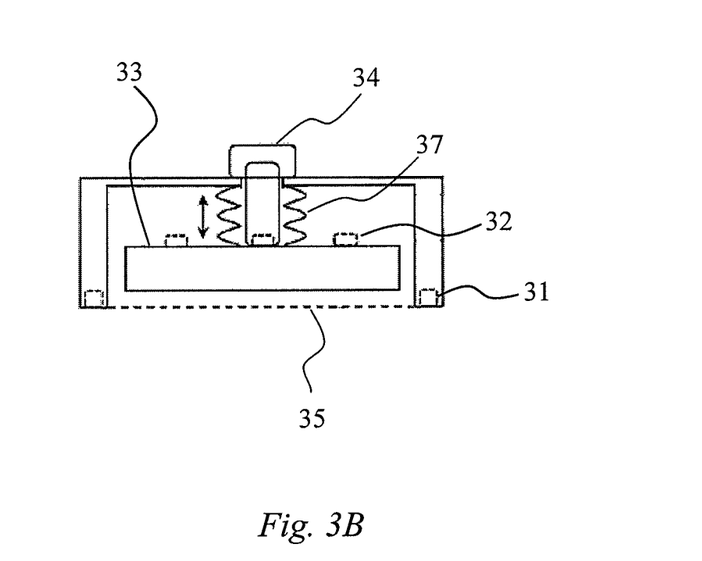
FIG. 3B is a cross-sectional view of the representative ultrasound probe in accordance with the principles of the present disclosure.

If the ultrasonic focal zone 36 incompletely falls within the adipose layer 39, the control system can control an actuator 34 as shown in FIG. 3B to move a therapeutic ultrasonic transducer 33 forward/backward along the depth, so the location of the ultrasonic focal zone 36 can be adjusted to completely fall within the adipose layer 39, as shown in FIG. 5.

The ultrasound sonication can be conducted while the ultrasonic focal zone 36 correctly and completely falls within the adipose layer 39. The ultrasound shot can be continuous HIFU or pulsed low-intensity low-frequency non-thermal ultrasound. During or after the ultrasonic treatment, the control system 25 generates an instruction of electrical stimulation to the electrical stimulator, and the electrical stimulator generates a signal to the electrode 26 to make passive exercise of muscle groups in any of thighs, shanks, arms, waist and back. In some embodiments, once the patient feels uncomfortable, the patient himself/herself can press the "emergency stop I" 27, and the system immediately terminates the ultrasound shot and the electrical stimulation, or alternatively, the operator presses the "emergency stop II" 28 to shut down the whole system to ensure the safety of the patient.

The above is explanation of the treatment plan and the usage of relevant elements. The further explanations of the elements are shown as follows.

FIG. 3A illustrates a bottom view of the ultrasound probe 24 of the present disclosure. At least four micro pressure sensors 31 are inlaid in fringe of the front terminal fringe of the probe to detect the pressure applied on skin. Said micro pressure sensors 31 are deployed with an interval of angle of 360/4N, where 4N denotes the number of the pressure sensor 31 and N is an integer. The therapeutic ultrasonic transducer 33 of the probe 24 is to produce HIFU or pulsed low-intensity low-frequency ultrasound, which is made of piezoelectric material with adaption of high electric voltage such as PZT4 piezo creamics, PZT8 piezo creamics, piezocomposite material and the like. A-mode ultrasonic transducers 32 detect eco signals from the interfaces between any tissues of skin 35, subcutaneous fat 39, muscle 40 and the like to construct depth and thickness of skin 35, subcutaneous fat 39 and muscle 40. A-mode ultrasonic transducers 32 are made of piezoelectric material with high electromechanical coupling factor. These 3 A-mode ultrasonic transducers 32 are arranged with equal interval to be integrated with the therapeutic ultrasonic transducer.

By positive-negative action of the actuator to move the therapeutic ultrasonic transducer 33 forward/backward in the depth direction as shown in FIG. 3B, the ultrasonic focal zone 36 completely falls within the adipose layer 39. In some embodiments, the therapeutic ultrasonic transducer 33 is immersed in the degassed pure water, and a membrane 35 is used to seal the front opening of the ultrasound probe 24 and an elastic tube 37 is used to isolate the degassing pure water and the actuator 34. Said membrane 35 is made of a material with adaption of water pressure in the ultrasound probe 24 and low attenuation to 3-MHz ultrasound.

Figure 3C:
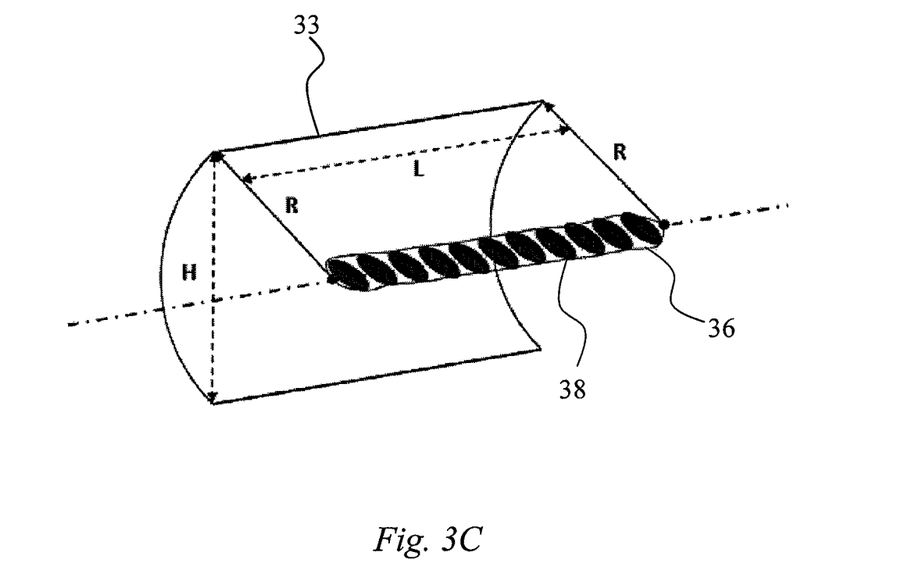
FIG. 3C is a schematic drawing illustrating the geometric structure and focusing characteristics of the representative therapeutic ultrasound transducer in accordance with the principles of the present disclosure.

FIG. 3C illustrates a structure of therapeutic ultrasonic transducer 33 and its focusing. Its geometric structure is a truncated cylinder with a radius of curvature R, a length L and an aperture diameter H, which is composed of a single piezoelectric element or a plurality of independent piezoelectric elements. While a signal of electrical phase being zero (0) is input to the therapeutic ultrasonic transducer 33, because of the restriction of the geometric structure, the ultrasound beams converge on an area at the central line of the cylinder to form a focal zone 36, wherein the focal zone 36 presents as a linear band. Several-6 dB peak intensity foci 38 are distributed in the line-shape focal zone 36. These foci 38 are rice-shape and are arranged in a line. The size of each focus can be determined by operation frequency of the therapeutic transducer 33 and the f-number (f-number is a ratio of R to H), for example, the width of the focus is positively linear correlation to the product of wave length and f-number, and the length of the focus is positively linear correlation to the product of wave length squared and f-number. The dimensions of the line-shape focal zone 36 can be determined by the length L of the therapeutic ultrasonic transducer 33 and the width and length of the focus. Accordingly, the ultrasound probe 24 with various performance specifications can be established based on the treating target, depth and area of the treating region, and the like for better therapeutic effects.

In clinical practice, the adhesive electrode pad is typically used for electrical stimulation, which can enlarge the contact area (e.g., 3×3 $cm^2$ for big muscle, and 2×2 $cm^2$ for small muscle) and reduce the current density. The electrical stimulator is generally operated at a constant-current mode. The stimulus is a periodical wave with tunable parameters such as wave duration, frequency, and amplitude. The range of stimulus parameters is often used to be 1-10 ms in wave width, 10-15 Hz at frequency, and 1-10 mA in current intensity. One of many recipes for electrical stimulation is for example, to only adjust the current intensity at the constant wave duration and frequency to regulate the strength and the displacement of muscle contraction. A microprocessor in the control unit can be programmed to control the stimulator and stimulus. While performing the ultrasonic treatment of adipose tissue and the electrical stimulation simultaneously, it can achieve energy consumption as well as introduction of released lipid molecules into the stimulated muscle. Stimulation sites can be tight quadriceps, shank gastrocnemius, or abdominal muscle, depending on the user's desires. The treatment time of electrical stimulation is about 30 minutes. After ultrasonic treatment, the electrical stimulation is still provided for several days, such as 30 minutes per time and two times per day, to continuously consume energy.

OTHER EMBODIMENTS

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A non-invasive system for destroying fat cells at a target region and accelerating metabolism of released lipids, comprising at least one focused ultrasound device, at least one electrical stimulation device configured to passively exercise at least one muscle, and a control unit, wherein:
the focused ultrasound device comprises:
a focused ultrasound probe comprising one or more ultrasound transducers with one or more piezoelectric elements to produce a line-shape focal zone;
a power amplifier; and
a probe holder for adjusting the location of a focal zone of the ultrasound transducer;
wherein the focused ultrasound device and the electrical stimulation device are configured to synergistically accelerate metabolism of lipids released from destroyed fat cells.

2. The non-invasive system for destroying fat cells and accelerating metabolism of released lipids of claim 1, wherein:
the at least one electrical stimulation device comprises:
one or more pairs of electrodes of electrical stimulation; and
an electrical stimulator with multi channels.

3. The non-invasive system for destroying fat cells and accelerating metabolism of released lipids of claim 1, wherein the focused ultrasound probe comprises one or more piezoelectric elements, which is driven by the power amplifier to output a high-intensity focused ultrasound (HIFU) or a non-thermal ultrasound.

4. The non-invasive system for destroying fat cells and accelerating metabolism of released lipids of claim 1, wherein the line-shape focal zone comprises more than 1 focus arranged in a line.

5. The non-invasive system for destroying fat cells and accelerating metabolism of released lipids of claim 1, wherein the focused ultrasound probe comprises four or more micro pressure sensors disposed in the front side of the probe.

6. The non-invasive system for destroying fat cells and accelerating metabolism of released lipids of claim 1, wherein the focused ultrasound probe comprises three or more A-mode ultrasonic transducers.

7. The non-invasive system for destroying fat cells and accelerating metabolism of released lipids of claim 1, the one or more pairs of electrodes is configured to provide electrical stimulation to a target muscle group to achieve a passive exercise.

8. The non-invasive system for destroying fat cells and accelerating metabolism of released lipids of claim 1, wherein the at least one muscle is remote from the target region.

9. The non-invasive system for destroying fat cells and accelerating metabolism of released lipids of claim 1, wherein the at least one muscle is selected based on its ability to consume ATP.

10. The non-invasive system for destroying fat cells and accelerating metabolism of released lipids of claim 1, wherein the at least one muscle comprises at least one muscle group of the thigh, shank, arm, abdomen, waist, and back.

11. The non-invasive system for destroying fat cells and accelerating metabolism of released lipids of claim 1, wherein the at least one muscle comprises at least one muscle group of the thigh.

12. A method of destroying fat cells and accelerating metabolism of released lipids, comprising steps of:
emitting a focused ultrasound to a target region of a subject to produce a line-shape focal zone, thereby destroying fat cells in an adipose tissue in the target region; and
providing an electrical stimulation to the subject to induce a passive exercise of a muscle group,
wherein the synergy of the focused ultrasound and the electrical stimulation accelerates metabolism of lipids released from destroyed fat cells.

13. The method of claim 12, wherein the focused ultrasound is a high-intensity focused ultrasound or a pulsed focused ultrasound.

14. The method of claim 12, wherein the electrical stimulation has a wave width of 1-10 ms, a frequency of 10-15 Hz, and a current intensity of 1-10 mA.

15. The method of claim 12, wherein the line-shape focal zone comprises more than one focus arranged in a line.

16. The method of claim 12, wherein the muscle group is remote from the target region.

17. The method of claim 12, wherein the muscle group comprises at least one muscle group of the thigh, shank, arm, abdomen, waist, and back.

18. The method of claim 12, wherein the muscle group comprises at least one muscle group of the thigh.

19. The method of claim 12, wherein the muscle group is selected based on its ability to consume ATP.

* * * * *